United States Patent [19]

Blewett

[11] Patent Number: 5,738,474
[45] Date of Patent: Apr. 14, 1998

[54] SURGICAL STAPLE AND STAPLE DRIVE MEMBER

[76] Inventor: Jeffrey J. Blewett, 86 Parkview Dr., Plantsville, Conn. 06479

[21] Appl. No.: 811,445

[22] Filed: Mar. 3, 1997

Related U.S. Application Data

[62] Division of Ser. No. 449,637, May 24, 1995, Pat. No. 5,630,540.

[51] Int. Cl.⁶ .................. F16B 15/02; A61B 17/08; A61D 1/00
[52] U.S. Cl. .................. 411/473; 411/920; 606/219
[58] Field of Search .................. 411/471, 472, 411/473, 457, 920; 606/143, 219

[56] References Cited

U.S. PATENT DOCUMENTS

| | | | |
|---|---|---|---|
| 2,741,147 | 4/1956 | Marano | 411/472 |
| 3,490,675 | 1/1970 | Green et al. | |
| 3,499,591 | 3/1970 | Green | |
| 4,396,139 | 8/1983 | Hall et al. | |
| 4,523,707 | 6/1985 | Blake, III et al. | |
| 4,607,638 | 8/1986 | Crainich | |
| 4,747,521 | 5/1988 | Brinkerhoff et al. | |
| 4,869,414 | 9/1989 | Green et al. | |
| 4,978,049 | 12/1990 | Green | |
| 5,040,715 | 8/1991 | Green et al. | |
| 5,222,975 | 6/1993 | Crainich | 606/219 |
| 5,269,792 | 12/1993 | Kovac et al. | |
| 5,364,003 | 11/1994 | Williamson, IV | |
| 5,366,479 | 11/1994 | McGarry et al. | 606/219 |
| 5,465,894 | 11/1995 | Clark et al. | |
| 5,630,540 | 5/1997 | Blewett | |

FOREIGN PATENT DOCUMENTS

| | | | |
|---|---|---|---|
| 7219687 | 11/1987 | Australia | |
| 652276 | 3/1993 | Australia | 606/219 |

Primary Examiner—Neil R. Wilson

[57] ABSTRACT

A surgical staple is provided which includes a bridge portion having at least two adjacent arcuate sections, each defining a constant radius of curvature along the arc length thereof. Transition portions are disposed at opposed end portions of the bridge portion, each having a curved profile. The surgical staple is further provided with legs having first end portions connected to the transition portions and second end portions extending therefrom. The surgical staple is constructed such that the legs move between an undeformed position substantially transverse to the bridge portion and a deformed position in which at least a portion of each of the legs is in approximation with the bridge portion. A drive member is also disclosed which is configured to urge a plurality of surgical staples from a staple cartridge when acted upon by an applied actuating force. The drive member has a support portion which complements the geometry of the bridge portion of the staple.

9 Claims, 6 Drawing Sheets

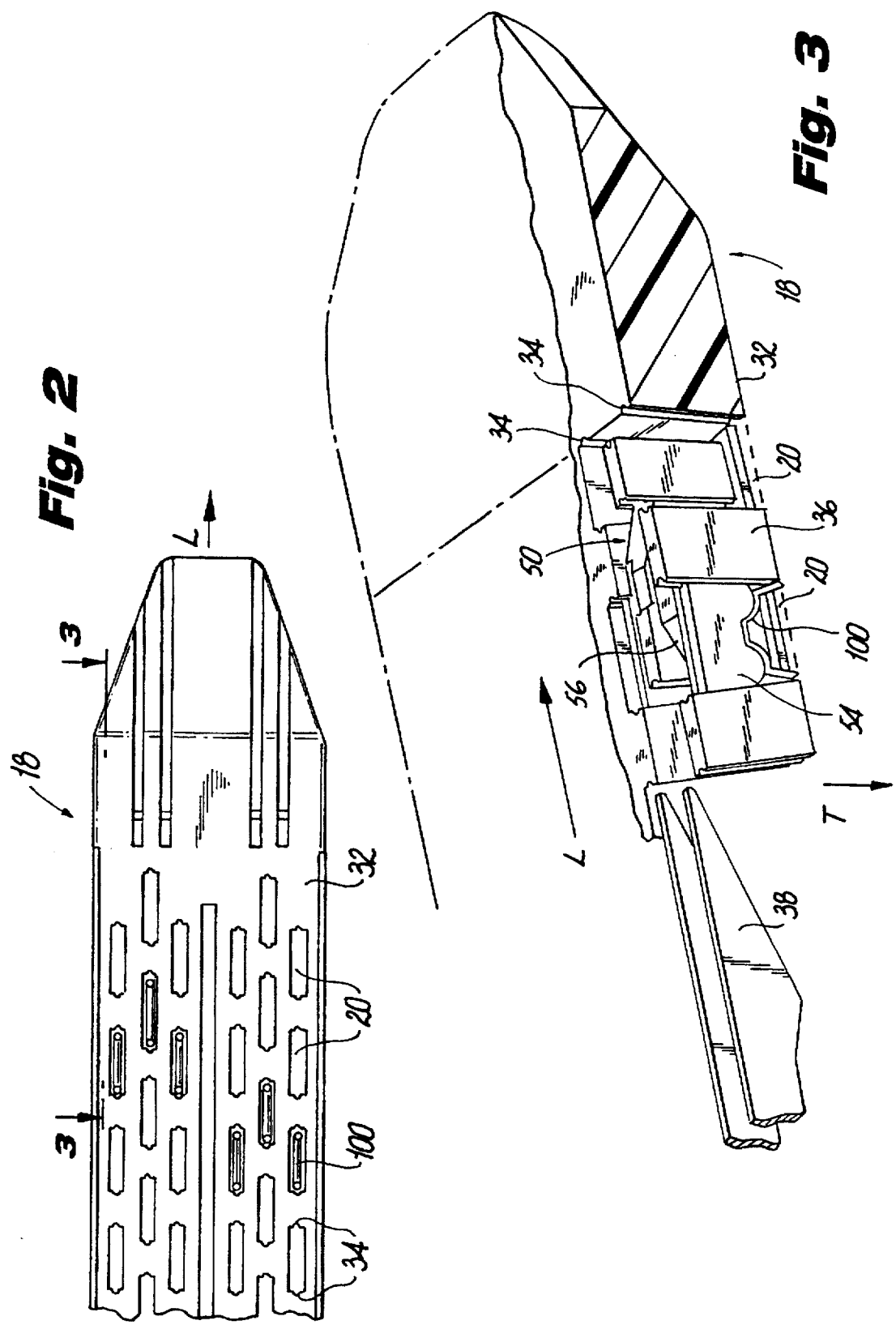

SURGICAL STAPLE AND STAPLE DRIVE MEMBER

This is a divisional of U.S. application Ser. No. 08/449,637 filed May 24, 1995, now U.S. Pat. No. 5,630,540.

BACKGROUND

1. Technical Field

The subject application relates to surgical stapling apparatus, and more particularly to a surgical staple and a drive member for driving a plurality of such staples from a cartridge assembly.

2. Background of Related Art

Surgical stapling apparatus are widely used in surgical procedures to fasten body tissue quickly and efficiently by driving fasteners or staples into the tissue. In certain types of staplers, a single staple is typically formed around an anvil, e.g., skin staplers, for approximating tissue. Such staplers may employ staples having a variety of configurations, as for example a conventional U-shaped configuration and variations thereon. See, e.g., U.S. Pat. No. 5,222,975 to Crainich.

In other types of staplers, such as those for mechanically stitching together hollow organs, the main linear drive, a cam member, moves longitudinally in a direction transverse to the direction the staples are to be driven. Typically, such staplers employ a number of staple drive members or pusher elements which pass through grooved slots of a staple retaining cartridge, such slots being arranged end-to-end in rows. Under normal operation, the longitudinally moving cam member passes into and through the cartridge, contacting cam surfaces on the drive members, thereby transversely pushing the drive members through the grooved slots. Thus, the drive members convert linear motion from the cam member to transverse staple motion. The rows of staples are thereby driven into the body tissue to be fastened.

An example of such an arrangement is described in commonly assigned U.S. Pat. No. 3,490,675 to Green et al. The drive member disclosed therein has a pusher plate, guide rails, and a V-shaped portion for contacting the driving cam. A further modification is illustrated in commonly assigned U.S. Pat. No. 3,499,591 to Green, which discloses a two staple driver capable of driving double rows of staples in a single cam stroke for greater holding strength than a single row. The two staple driver includes two drive sections in separate planes, with a v-shaped top surface for contacting the pusher cam. Each staple pair is staggered longitudinally (i.e., each staple is positioned diagonally behind the other, in a zig-zag fashion) and bridges the push-bar path. When the two staple drivers eject the pair of staples to engage tissue, the forces generated tend to be balanced in both the side-to-side and front-to-back directions, thereby decreasing any offset loading on the pushers.

U.S. Pat. No. 4,978,049 to Green discloses a staple drive member for applying three parallel rows of staples in a single election action and in staggered overlapping arrangement. The staple driver member disclosed therein comprises three pusher plates oriented in a staggered arrangement such that two outside plates are located predominantly at the proximal end, and one middle plate is located predominantly at the distal end. This configuration effectively balances the forces applied to the drive member when ejecting staples. Such a configuration also permits the application of a relatively smooth ejection force throughout the stapling operation. See also commonly assigned U.S. Pat. Nos. 5,040,715 and 4,978,049.

Each of the above-mentioned staple systems are commonly employed to drive conventional U-shaped staples having two opposed legs connected by a linear bridge. Therefore, the staple drivers have flat surfaces to correspond to the linear bridge portions of the staples. When deformed, such staples tend to form a B-shape, wherein the legs are curved towards the bridge and the chiseled end points are in a position to re-puncture the tissue being sutured. In such an orientation, a significant area of the deformed leg portions are not in extensive contact with the tissue. It would be desirable, therefore, to provide a staple which, when deformed, secures tissue along a greater length of the leg portions thereof and which does so with a reduced tendency to re-puncture the tissue being secured.

SUMMARY

The subject application is directed to a unique surgical staple which includes a bridge portion having at least two adjacent arcuate sections, each defining a constant radius of curvature along the arc length thereof. Transition portions are disposed at opposed end portions of the bridge portion, each having a curved profile. The surgical staple is further provided with legs having first end portions connected to the transition portions and second end portions extending therefrom. The surgical staple is constructed such that the legs move between an undeformed position substantially transverse to the bridge portion and a deformed position in which at least a portion of each of the legs is in approximation with the bridge portion. Preferably, in the deformed position, the legs assume a curved configuration which substantially complements the curvature of the arcuate sections of the bridge, contacting tissue along their entire arc length.

The subject application is also directed to a cartridge assembly for a surgical stapler which includes a cartridge body defining a plurality of slots elongated along a longitudinal axis. Each slot supports a surgical staple having a bridge portion including at least two arcuate sections defining a constant radius of curvature along the arc length thereof. The cartridge assembly is further provided with a plurality of staple drive members disposed within the cartridge body and positioned adjacent the staples. Each of the staple drive members has at least one pusher element including a curvilinear support portion for supporting the bridge portion of the staple. Each of the drive members is configured to eject the staples from the slots when acted upon by an actuating force, e.g., a longitudinally moving cam member which travels into and through the staple cartridge.

The unique surgical staple and cartridge assembly provide numerous clinical advantages. Of particular note, in highly vascular and/or thin tissue applications, e.g., the mesentery, the staple/cartridge disclosed herein provides advantageous hemostasis in an efficient and efficacious manner. The final shape of the staple disclosed herein, rather than forming a "B-shape" as in conventional staples, offers hemostasis comparable to that achieved with prior art clips, and particularly vascular clips, sutrues or cautery, while significantly reducing the time and effort required to achieve such hemostasis.

The unique surgical staple and cartridge assembly may be used in a variety of applications, e.g., endoscopic or non-endoscopic procedures, and may be incorporated into instruments that only staple or both staple and ligate. The length of the staple line and the size of the staple in the pre-formed and formed conditions may be varied depending on the surgical application. For example, the staple and cartridge may be configured and dimensioned to be used in conjunction with commercially available instruments such as the Endo GIA* or Endo TA* 30 and 60 surgical stapling instruments commercially available from the assignee of the present application.

These and other features of the staple and drive member will become more readily apparent to those skilled in the art from the following detailed description of the subject application.

BRIEF DESCRIPTION OF THE DRAWINGS

Various embodiments of the subject staple and staple drive member are described herein with reference to the drawings wherein:

FIG. 2 is a top elevational view of the tissue-contacting surface of a staple cartridge assembly used in conjunction with a stapling apparatus, such as that illustrated in FIG. 1.;

FIG. 3 is a perspective view in partial cross-section, from below, of the staple cartridge assembly, taken along line 3—3 of FIG. 2, with the staple and staple drive member of the subject application positioned therein;

DETAILED DESCRIPTION OF PREFERRED EMBODIMENTS

Figure 1:
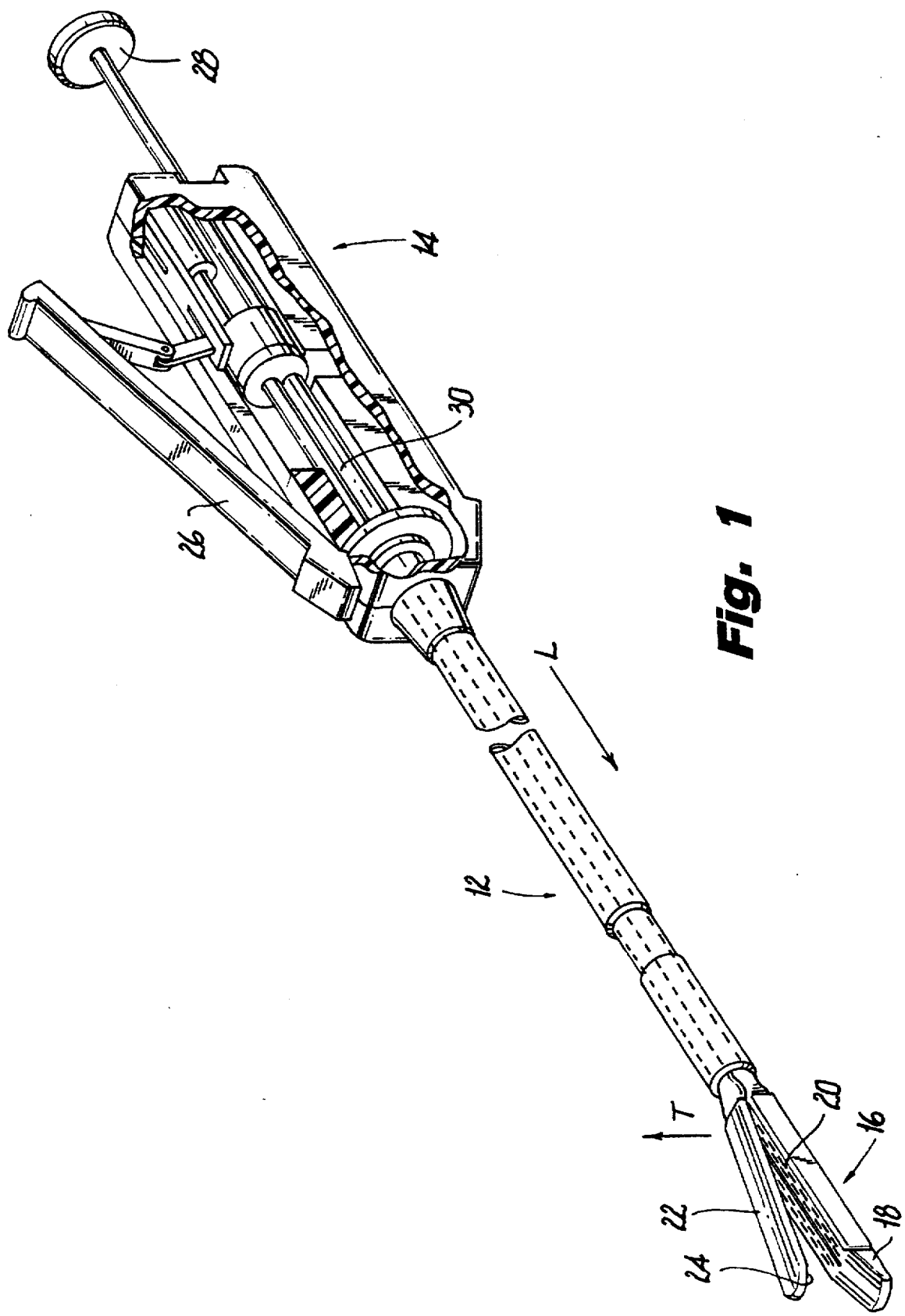
FIG. 1 is a perspective view in partial cross-section of a surgical stapling apparatus which is to be used in conjunction with the staple and the staple drive member constructed in accordance with a preferred embodiment of the subject application.

Surgical stapling apparatus employing staple drive members such as those described hereinbelow are disclosed in commonly assigned U.S. Pat. No. 4.978.049 to Green, and U.S. Pat. Nos. 5.040.715 and 5.318.221 to Green et al., all of which are incorporated by reference herein.

In the drawings and in the description which follows, the term "proximal", as is traditional, will refer to the end of the apparatus which is closest to the operator, while the term distal will refer to the end which is furthest from the operator. The terms "vertical" and "downward" are used relatively to refer to a direction transverse to the longitudinal direction shown in the drawings.

The present apparatus shall be discussed in terms of endoscopic procedures and apparatus. However, use herein of terms such as "endoscopic", should not be construed to limit the present application to an apparatus for use only in conjunction with an endoscopic tube. To the contrary, it is believed that the present apparatus may find use in conventional, open surgery as well as procedures where access is limited to arthroscopic or laparoscopic procedures.

A surgical stapling apparatus for use in conjunction with the subject staple drive member and staple is illustrated in FIG. 1, and is designated generally by reference number 10. Preferred surgical stapling apparatus for use therewith are commercially available from the assignee of the present application under the trade names Endo GIA* and Endo TA*. Surgical stapler 10 includes an endoscopic portion 12 and a handle portion 14. The endoscopic portion 12 is configured to be inserted into the body through a narrow diameter opening or cannula. The distal portion of the endoscopic portion 12 includes a first jaw 16 supporting a cartridge assembly 18 containing a plurality of elongated slots 20 for storing staples and staple drive members therein. A second jaw 22 includes an anvil 24 on an inner surface thereof. The second jaw 22 is movably mounted to the endoscopic portion 12 in order to clamp tissue between the anvil 24 and a tissue engaging surface of the cartridge assembly 18.

The handle portion 14 includes a lever 26 which enables the surgeon to remotely actuate jaws 16 and 22 by a known mechanical linkage. A plunger type handle 28 is used to advance drive bar 30 along the longitudinal axis of the apparatus 10 as indicated by arrow "L". One or more pusher cams are connected to drive bar 30 and advance simultaneously therewith relative to cartridge assembly 18 in order to drive a plurality of staple drive members which are positioned within slots 20 adjacent the staples. The staple drive members eject the staples from the cartridge assembly 18 in a direction substantially transverse to the longitudinal axis "L" and indicated by arrow "T". The ejected staples penetrate body tissue and are formed against the anvil 24 of second jaw 22.

The cartridge assembly 18, as shown in FIG. 2, includes a cartridge body 32 for supporting and storing the staple drive members and staples. A portion of staples 100 are shown prior to ejectment disposed within slots 20. The plurality of slots 20 formed in the tissue engaging surface of cartridge body 32 are elongated along longitudinal axis "L" and disposed in a series of parallel rows. A proximal and distal end of each slot 20 is provided with a groove 34 to stabilize the staple drive members as will be described below.

As shown in FIG. 3, a series of upright posts 36 are disposed in longitudinal rows between the elongated slots 20 (partially indicated in phantom). The staple drive member of the present application, which is indicated generally by reference numeral 50, is configured to slide transversely, as indicated by the arrow "T", between the upright posts 36. The grooves 34 provided at the proximal and the distal portions of slots 20 extend transversely along the height of the upright posts 36 and are intended to cooperate with guide rails (see, FIGS. 6–7) formed on the proximal and distal portions of pusher plates 54 of the staple drive members 50 in order to stabilize and guide drive member 50 during transverse motion. The surgical staple 100 of the subject application, which is particularly constructed for use in conjunction with drive member 50 is disposed adjacent pusher plate 54 within slot 20. A pusher cam, such as the double-bladed cam 38, moves longitudinally as indicated by arrow "L" in conjunction with drive bar 30 into cartridge assembly 18 to contact a proximal camming surface 56 of the staple drive member 50, thereby impelling drive member 50 transversely and ejecting staples 100 from slot 20. Cartridge assembly 18 is provided with a plurality of drive members 50 and staples 100 which are sequentially fired following a single stroke of cam 38.

Figure 4:
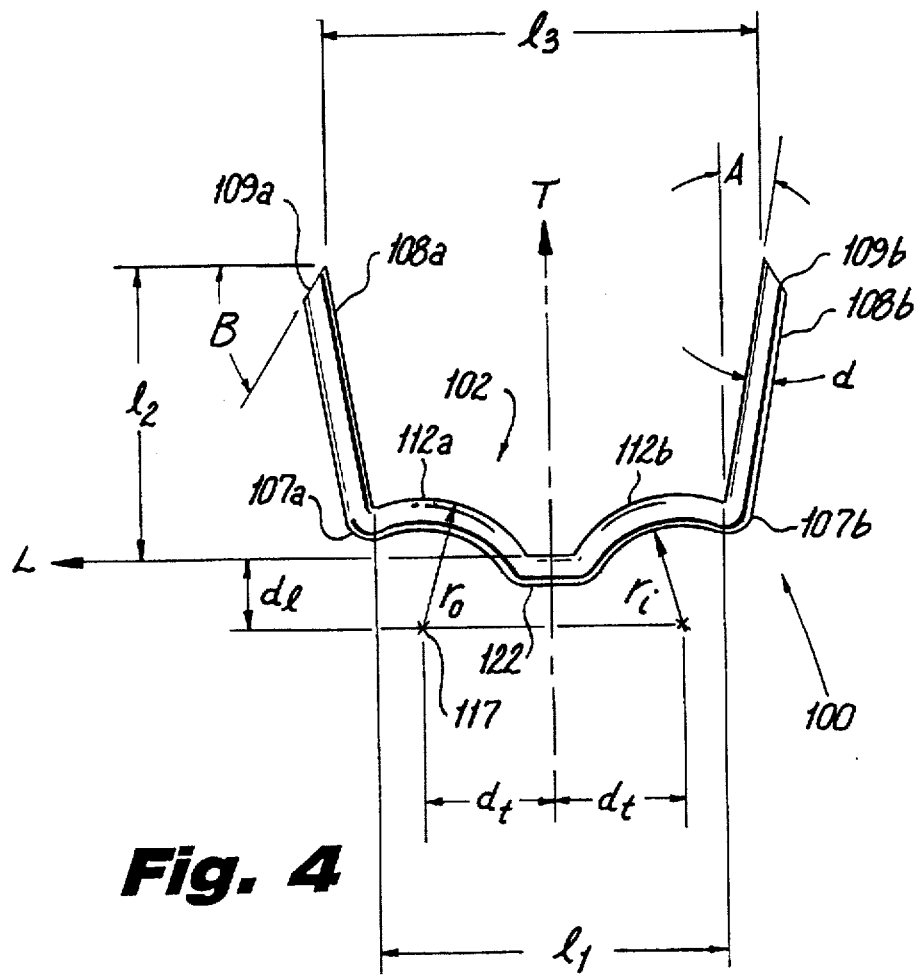
FIG. 4 is an elevational view of a surgical staple constructed in accordance with a preferred embodiment of the subject application.
Figure 5:
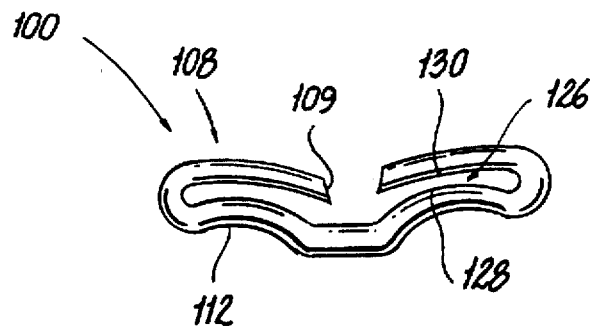
FIG. 5 is an elevational view of the surgical staple shown in FIG. 4 in a deformed condition wherein the leg portions are compressed in approximation with the bridge portion of the staple.
Figure 11:
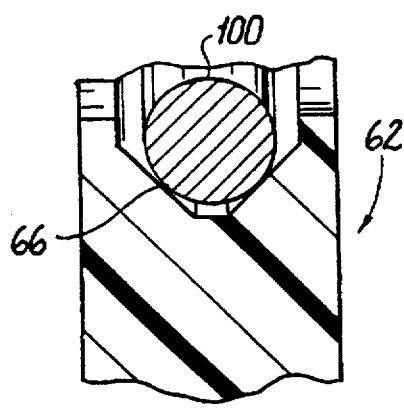
FIG. 11 is a cross-sectional view of the staple supporting portion of the staple drive member and the staple, taken along line 11—11 of FIG. 9.

Referring now to FIGS. 4 and 5, there is shown in an unformed and a deformed state a surgical staple constructed in accordance with a preferred embodiment of the subject application and designated generally by reference numeral 100. Surgical staple 100 may be formed from wire, such as stainless steel, titanium, or other similar material suitable for surgical utilization. Preferably, the staple cross-section is substantially circular (as shown in FIG. 11) and has a diameter "d" of approximately 0.0085 inch. Alternatively, shaped wire having oval, rectangular, semicircular or other cross-sectional configurations can also be utilized to construct the staples.

Staple 100 is symmetrical about transverse axis "T" and has a bridge portion indicated generally at 102 which is substantially aligned with longitudinal axis "L" and has a length "$l_1$" of approximately 0.101 inch. Slightly curved transition positions 107a, 107b are integrally formed with bridge 102 and are disposed at end portions thereof. A pair of legs 108a, 108b each have a first portion connected to the transition portions 107a, 107b respectively. The legs extend in a substantially transverse direction, terminating with second end portions in chiseled points 109a, 109b. The legs extend for a length "$l_2$" of approximately 0.083 inch along transverse axis "T". At least two arcuate portions 112a, 112b are integrally formed as part of bridge portion 102, and have a constant inner radius "$r_i$" and a constant outer radius "$r_o$" along the arc length thereof. Arcuate portions 112a, 112b correspond to the shape of pusher plates 54 of staple drive member 50 (see FIG. 7,9).

The present surgical staple 100 has an inner radius "$r_i$" of 0.028 inch and an outer radius "$r_o$" of 0.037 inch. Both radii are swept from a point 117 located a distance "$d_t$" of 0.037 inch from transverse axis "T" and a longitudinal distance "$d_l$" of 0.020 inch from longitudinal axis "L" in a direction opposite the legs 108a, 108b. Bridge portion 102 is further provided with a substantially linear medial crown portion 122, which is aligned with longitudinal axis "L" and disposed between arcuate sections 112a, 112b. The dimensions of staple 100 may be modified to correspond to the particular surgical application and the configuration of the particular cartridge assembly used therewith. For example, variations in tissue thickness generally requires a proportional increase in the length "$l_2$" of legs 108a, 108b. Alternatively, the bridge portion 102 may be fabricated such that the arcuate sections 112a, 112b are abutting, thereby eliminating the linear crown section 122.

In order to penetrate body tissue effectively without collapsing inward prematurely, the legs 108a, 108b form an angle "A" of 8° with transverse axis "T". Consequently, the second end portions of legs 108a, 108b define a lateral spacing "$l_3$" of 0.125 inch, which is greater than the spacing "$l_1$" of 0.101 inch at the junction of the first end portions of legs 108a, 108b with the transition portions 107a, 107b. Furthermore, the chiseled points 109a, 109b form an angle "B" of preferably 57° with longitudinal axis "L", although different orientations of the legs 108a, 108b and points 109a, 109b are contemplated.

The angle "A" of legs 108a, 108b with respect to transverse axis "T" and the angle "B" of the chiseled points 109a, 109b with respect to longitudinal axis "L" are selected such that the action of driving staple 100 into anvil 24 (FIG. 1) curves the legs 108a, 108b into the configuration shown in FIG. 5. During formation, the second end portions of legs 108a, 108b are brought into approximation with arcuate portions 112a, 112b by bending legs 108a, 108b at transition portions 107a, 107b. The geometric configuration of arcuate sections 112a, 112b and the complementary curvature of legs 108a, 108b contributes to an extended contact region 126 with respect to the tissue being stapled. Contact region 126 includes a surface 128 of arcuate sections 112a, 112b, and a surface 130 of legs 108a, 108b. Furthermore, in the deformed position illustrated in FIG. 5, the chiseled points 109a, 109b are substantially parallel to arcuate portions 112a, 112b rather than in an intersecting relationship, thereby reducing unnecessary repuncture of tissue.

Figure 6:
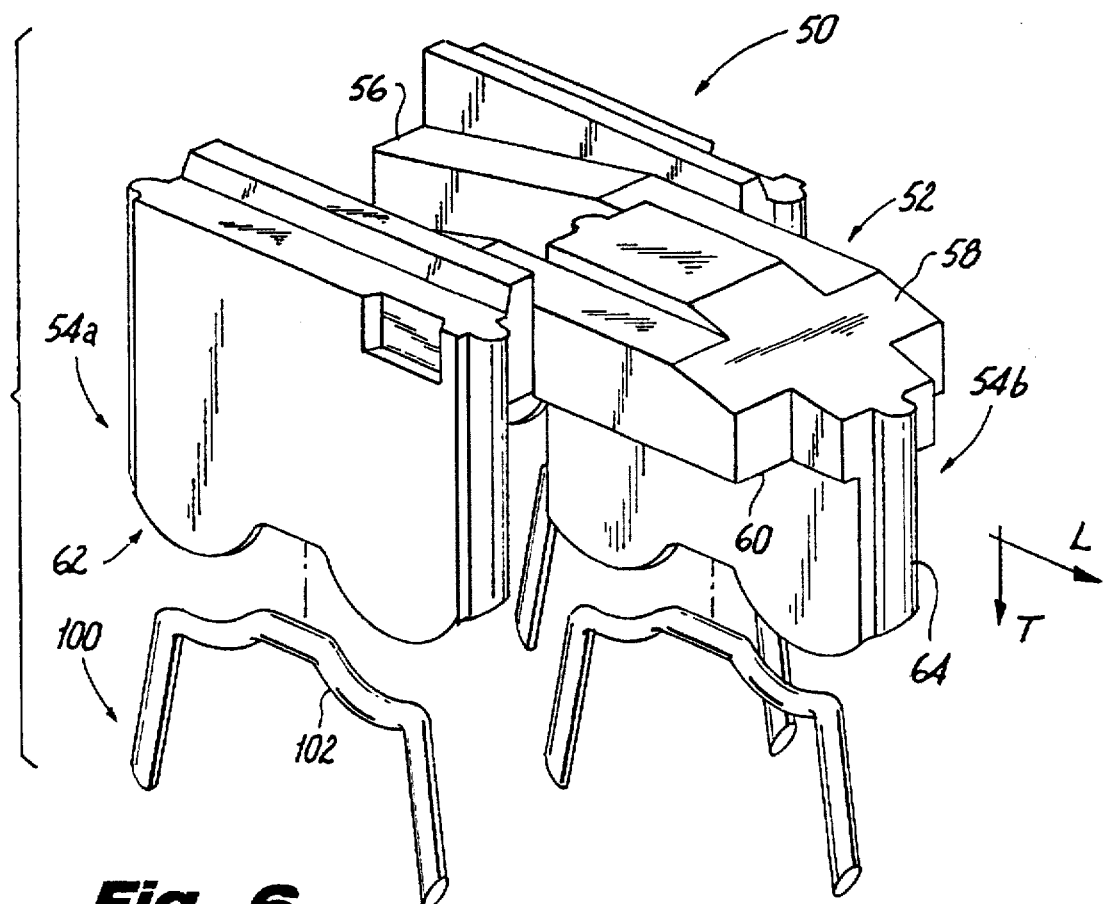
FIG. 6 is a perspective view from below of a staple drive member constructed in accordance with a preferred embodiment of the subject application, and a plurality of staples.
Figure 7:
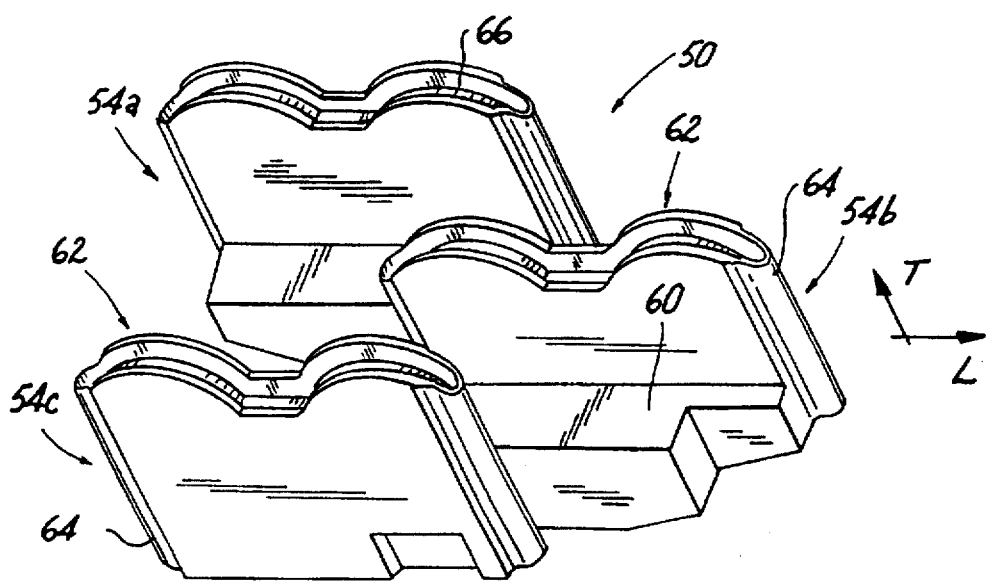
FIG. 7 is a perspective view from above of the staple drive member of FIG. 6.

Referring now to FIGS. 6 and 7, the staple drive member 50 includes a body portion 52 elongated longitudinally and three pusher plates 54a, 54b, 54c joined to body portion 52 and extending transversely therefrom. The drive member 50 may be injection molded as an integral unit from a high strength polymeric resin, such as DELRIN™ acetal. The drive member 50 may be constructed of any size which is appropriate to its function of driving staples. Typically, such drive members configured for use in conjunction with cartridge assembly 18 for endoscopic procedures are between 0.1 and 0.2 inches in length, about 0.075 inches in height, and about 0.10 to 0.15 inches in width.

Figure 8:
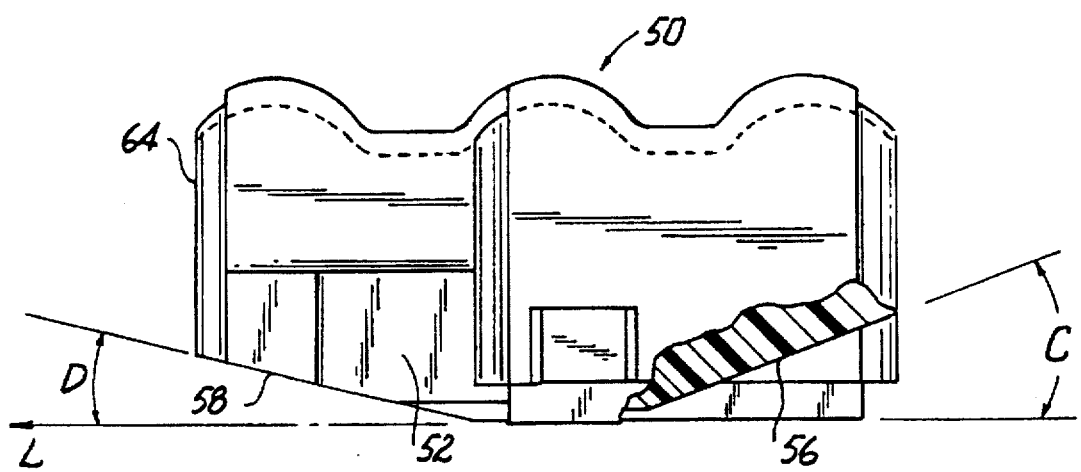
FIG. 8 is a side view in partial cross section of the staple drive member of FIG. 6, illustrating camming surfaces provided therein.
Figure 12:
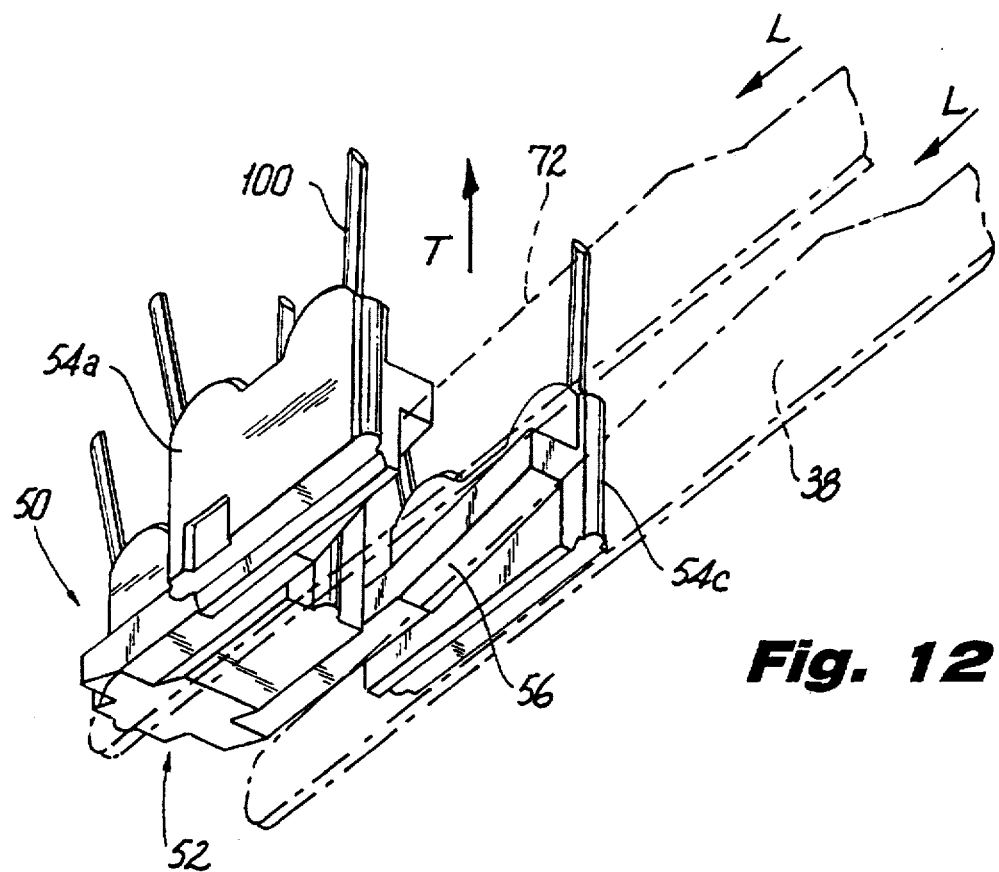
FIG. 12 is a perspective view from below of the staple drive member in conjunction with pusher cams.
Figure 13:
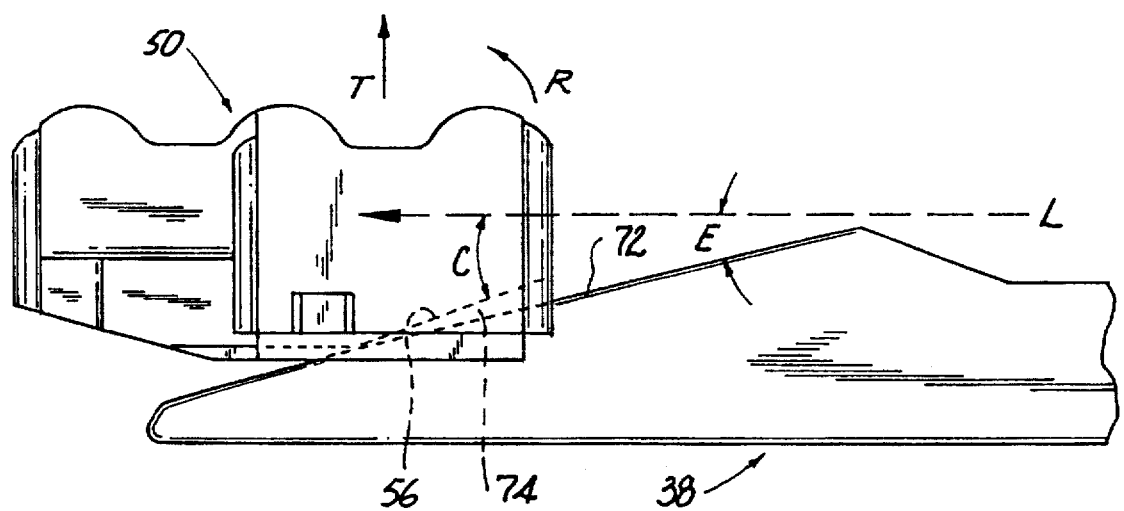
FIG. 13 is a side elevational view of the staple drive member and pusher cam.

Body portion 52, as illustrated in FIGS. 6 and 8, includes inclined camming surfaces 56 formed at the proximal end thereof and defining an angle "C" with the longitudinal axis "L" for contacting the longitudinally moving pusher cams 38 (see FIGS. 12–13). A distal inclined camming surface 58 defines an angle "D" with the longitudinal axis "L". Distal camming surface 58 inhibits jamming of the staple drive member 50 within the cartridge body 32 by permitting the camming blade 38 to slide over drive member 50 as the blade 38 is returned proximally to its starting position. A restraining surface 60 on the bottom surface of the body portion 52 prevents the staple drive member 50 from being ejected from the cartridge assembly 18 during staple application by abutting the inside surface of cartridge body 32 (See, FIG. 2).

The three parallel pusher plates 54a, 54b, and 54c each have a substantially rectangular cross-section and a staple supporting portion 62, as shown in FIGS. 6–11. Pusher plates 54a, 54b and 54c define three separate planes, each parallel to the longitudinal axis "L" of stapling apparatus 10 and are aligned in the direction of motion of cam 38, as best seen in FIG. 7. Furthermore, pusher plates 54a, 54b and 54c are staggered in orientation with respect to each other. The two outside pusher plates 54a and 54c are laterally aligned with each other at the proximal end of body portion 52, each one disposed at one of two sides of body portion 52. Middle pusher plate 54b is displaced from lateral alignment with side pusher plates 54a and 54c, and has an end aligned with the distal end of body portion 52.

Pusher plates 54a, 54b and 54c each have guide rails 64 on the proximal and distal ends thereof, extending from the staple supporting portion 62 to the bottom of the pusher plate, and serve to align and guide the staple drive member 50 within grooves 34 of cartridge body 32 (See, FIG. 3).

Figure 9:
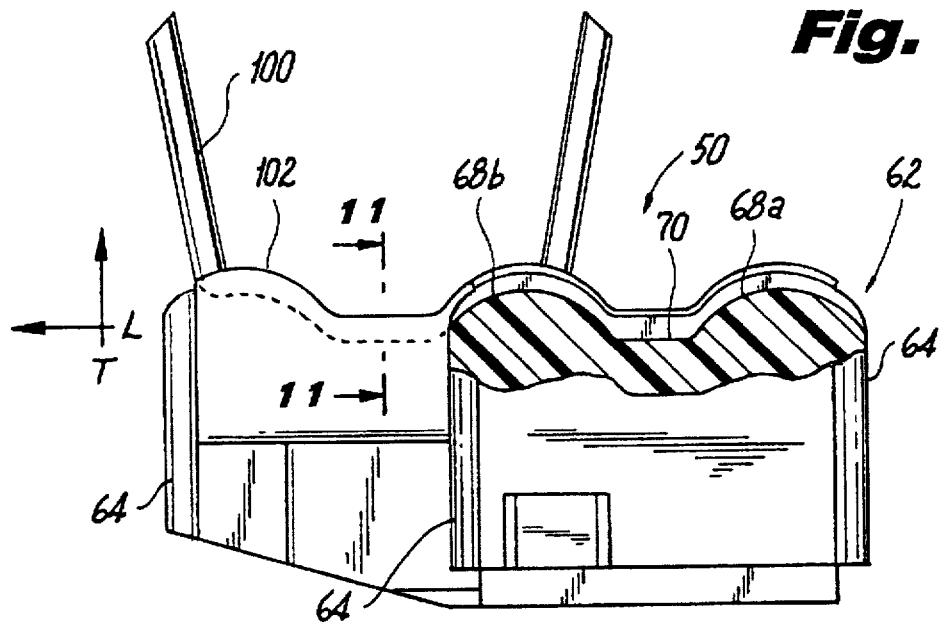
FIG. 9 is a side view in partial cross section of the staple drive member of FIG. 6, illustrating a staple supporting portion and the staple used in conjunction therewith.
Figure 10:
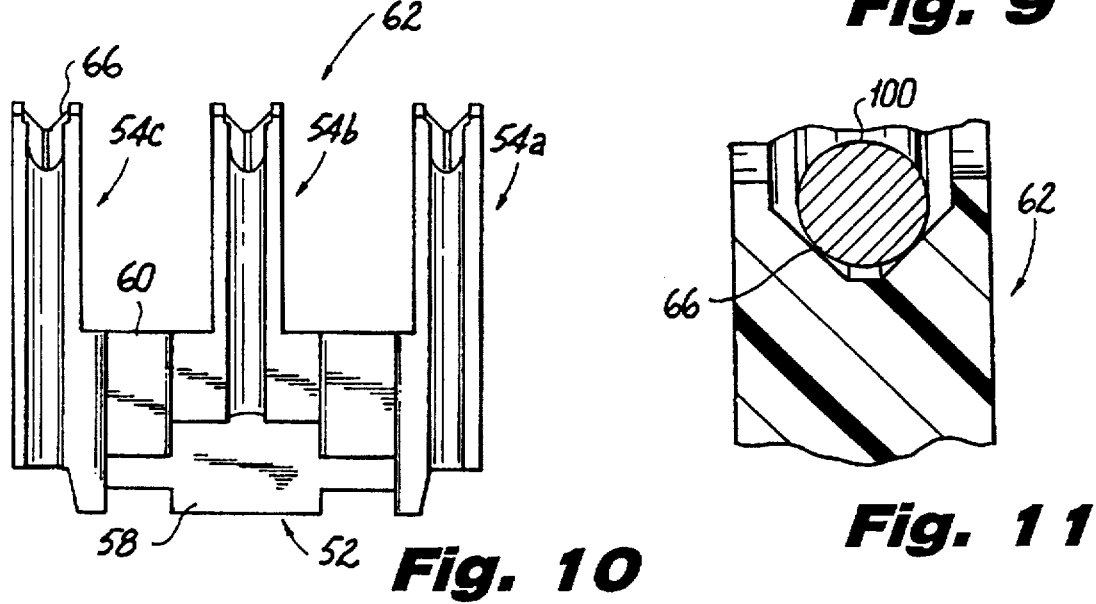
FIG. 10 is a front elevation view of the staple drive member of FIG. 6.

As best seen in FIGS. 7 and 11, the staple supporting portion 62 of each of pusher plates 54a, 54b and 54c has a staple cradling notch 66 extending longitudinally along the edge thereof which contacts bridge portion 102 of the surgical staple 100 associated therewith. Notch 66 has a generally V-shaped cross-sectional configuration to firmly support the staple bridge 102. The supporting portion 62, as illustrated in FIGS. 7 and 9, further has a curvilinear profile which complements the shape of a bridge portion 102 of the surgical staple 100 (See, FIG. 4) in order to evenly distribute forces across the bridge portion 102 during application of the staple 100 through tissue and against anvil 24. Specifically, staple supporting portion 62 includes a pair of convex portions 68a, 68b disposed between proximal and distal guide rails 64. As illustrated in FIG. 9, staple supporting portion 62 further includes a linear portion 70 substantially aligned with longitudinal axis "L" of surgical stapling apparatus 10 and disposed between convex portions 68a, 68b to support the medial crown portion 122 of staple 100.

Referring now to FIGS. 12 and 13, the staple drive member 50 is oriented with respect to pusher cams 38, (indicated in phantom) such that a contact edge 72 of pusher cam 38 contacts proximal camming surface 56 in order to transfer longitudinal motion of cam 38, indicated by arrow "L", to transverse motion "T". As illustrated in FIG. 13, the contact edge 72 of cam 38 may induce a transverse motion "T" as well as some undesired torque in the staple drive member 50 in the direction of arrow "R". This torque may attempt to rotate staple drive member 50 within grooved slots 34. The configuration of the present apparatus advantageously reduces the potential effect of the torque force on staple drive member 50. First, the angle "E" between the contact edge 72 of the pusher cam 38 and the longitudinal direction of travel "L" is smaller than the angle "C" between the proximal camming surface 56 of staple member 50 and direction of travel "L". As a result of selecting an angle "E" smaller than angle "C", space 74 is created between contact edge 72 and camming surface 56 which permits rotation of the drive member 50 relative to the cam 38 in a direction opposite that of the pusher cam-induced rotation. Second, two outside pusher plates 54a, 54c located at the proximal portion of drive member 50 also counter the potential torque. Upon engagement with tissue, outer plates 54a, 54c offer greater resistance at the proximal portion than does the single plate 54b disposed at the distal portion, thereby creating a torque in the direction opposite that of the pusher cam-induced torque.

It will be understood that various modifications may be made to the embodiments disclosed herein. Therefore, the above description should not be construed as limiting, but merely as exemplifications of preferred embodiments. For example, the subject invention, which has been described with respect to a surgical apparatus wherein the staples are fired transverse to the longitudinal axis, may alternatively be described with respect to an apparatus wherein the staples are driven longitudinally against an anvil having a staple forming surface extending transversely and disposed opposite to the staples. Those skilled in the art will envision other modifications within the scope and spirit of the claims appended hereto.

What is claimed is:

1. A surgical staple comprising:
   a) a bridge portion having at least two adjacent arcuate sections, each defining a constant radius of curvature along an arc length thereof;
   b) transition portions disposed at opposed end portions of the bridge portion each having a curved profile and defining a first lateral spacing therebetween; and
   c) legs having first end portions connected to the transition portions and second end portions extending therefrom defining a second lateral spacing therebetween, wherein the second lateral spacing is at least equal to the first lateral spacing, the staple being constructed such that the legs are adapted to be moved between an undeformed position substantially transverse to the bridge portion and a deformed position in which at least a portion of each of the legs is in approximation with the bridge portion.

2. The surgical staple of claim 1, wherein each of the legs in the undeformed position defines an angle of between 90° and 100° with an axis extending parallel to the bridge portion.

3. The surgical staple of claim 1, which further comprises tissue contacting surfaces defined along the arcuate sections and on each of the legs in approximation with the bridge portion in the deformed position, the legs having a curved configuration which substantially complements the curvature of the arcuate sections.

4. The surgical staple of claim 1, wherein the second end portion of each of the legs is provided with a chiseled point.

5. The surgical staple of claim 4, wherein the chiseled point of each of the legs defines an angle of between 50° and 60° with an axis extending parallel to the bridge portion.

6. The surgical staple of claim 4, wherein the chiseled point of each of the legs in the deformed position is directed substantially parallel to the curvature of the arcuate sections.

7. The surgical staple of claim 1, wherein the bridge portion further comprises a medial crown portion disposed between the arcuate portions.

8. The surgical staple of claim 7, wherein the medial crown portion is substantially linear and is disposed outwardly in a direction opposite the second end portions of the legs in the undeformed position.

9. The surgical staple of claim 1, wherein the staple is formed of a material selected from the group consisting of titanium and stainless steel.

* * * * *